(12) United States Patent
Bigus et al.

(10) Patent No.: US 6,540,719 B2
(45) Date of Patent: Apr. 1, 2003

(54) CATHETER WITH ROTATABLE BALLOON

(75) Inventors: Stephen J. Bigus, San Jose, CA (US); Phebe T. Cababaro, San Jose, CA (US); Steven B. Choi, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 46 days.

(21) Appl. No.: 09/733,119

(22) Filed: Dec. 8, 2000

(65) Prior Publication Data

US 2002/0072755 A1 Jun. 13, 2002

(51) Int. Cl.[7] ............................................. A61M 29/00
(52) U.S. Cl. ................................................. 604/96.01
(58) Field of Search ........................ 604/280, 96, 103, 604/101, 95; 606/192, 194; 623/1.35, 1.11

(56) References Cited

U.S. PATENT DOCUMENTS

| | | | |
|---|---|---|---|
| 5,055,109 A | 10/1991 | Gould et al. | 604/95 |
| 5,279,561 A | 1/1994 | Roucher et al. | 604/96 |
| 5,312,340 A | 5/1994 | Keith | 604/96 |
| 5,397,305 A | 3/1995 | Kawula et al. | 604/96 |
| 5,593,419 A | 1/1997 | Segar | 606/194 |
| 5,868,777 A | 2/1999 | Lam | 606/194 |
| 5,919,163 A | 7/1999 | Glickman | 604/101 |
| 6,165,195 A | 12/2000 | Wilson et al. | 606/194 |

*Primary Examiner*—Henry Bennett
*Assistant Examiner*—Sabrina Dagostino
(74) *Attorney, Agent, or Firm*—Fulwider Patton Lee & Utecht, LLP (57) ABSTRACT

An intraluminal catheter having a catheter shaft and distal member rotatable relative to at least a section of the catheter shaft. In one embodiment, the catheter has a catheter shaft, a distal member, which in a presently preferred embodiment is a balloon mounted on a distal portion of the shaft, and a tubular sealing member having an expandable portion disposed at least in part within a section of the distal member. The tubular sealing member has an expanded configuration, and an unexpanded configuration expandable into contact with the section of the distal member, so that the distal member is rotatable relative to at least a section of the catheter shaft and to the tubular sealing member when the tubular sealing member is in the unexpanded configuration.

30 Claims, 4 Drawing Sheets

CATHETER WITH ROTATABLE BALLOON

BACKGROUND OF THE INVENTION

This invention generally relates to intravascular catheters, such as balloon catheters used in percutaneous transluminal coronary angioplasty (PTCA), stent delivery, and drug delivery.

PTCA is a widely used procedure for the treatment of coronary heart disease. In this procedure, a balloon catheter is advanced into the patient's coronary artery and the balloon on the catheter is inflated within the stenotic region of the patient's artery to open up the arterial passageway and thereby increase the blood flow there through. To facilitate the advancement of the catheter into the patient's coronary artery, a guiding catheter having a preshaped distal tip is first percutaneously introduced into the cardiovascular system of a patient by the Seldinger technique through the brachial or femoral arteries. The guiding catheter is advanced until the preshaped distal tip of the guiding catheter is disposed within the ascending aorta adjacent the ostium of the desired coronary artery, and the distal tip of the guiding catheter is then maneuvered into the ostium. A balloon catheter may then be advanced through the guiding catheter into the patient's coronary artery over a guidewire until the balloon on the catheter is disposed within the stenotic region of the patient's artery.

The balloon is inflated to open up the arterial passageway and increase the blood flow through the artery. Generally, the inflated diameter of the balloon is approximately the same diameter as the native diameter of the body lumen being dilated so as to complete the dilation but not over expand the artery wall. After the balloon is finally deflated, blood flow resumes through the dilated artery and the dilatation catheter can be removed therefrom.

In a large number of angioplasty procedures, there may be a restenosis, i.e. reformation of the arterial plaque in the dilated arterial region. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the expanded stent is left in place within the artery. Stents with at least one end being nonperpendicular to the longitudinal axis, or angulated stents, have been proposed for use at the opening to an ostial branch of a main body lumen. Use of an angulated stent allows the expanded stent to match the arterial geometry, so that the entire stenosed region can be covered without the stent projecting into the main artery.

However, proper delivery and placement of an angulated stent is difficult, because the stent must be properly orientated to match the branch opening in the main artery wall, which may require rotation of the contracted stent mounted on the balloon before the stent is expanded. With conventional stent delivery systems, the distal section of the catheter within the body lumen is rotated by torquing the proximal section of the catheter which extends out of the patient. However, the torque applied to the proximal end of the catheter is not always transmitted to the distal end of the catheter due to frictional engagement within the guiding catheter and within the patient's artery wall distal to the guiding catheter, and the mechanical loss from the tortuosity of the vessel. This causes an energy build up in the catheter, and any torque that is transmitted yields unpredictable results, leading to a lack of control over the catheter. The catheter may twist along its shaft, and a sudden release of the frictional engagement can cause the catheter shaft to untwist and the distal end "whip" within the lumen. In other instances, the catheter does not untwist at all, and it may become so twisted that damage may occur to the catheter shaft. Therefore, the control needed to correctly orient an angulated stent does not exist.

Therefore, it would be a significant advance to provide a catheter with improved control over the orientation of the catheter distal end.

SUMMARY OF THE INVENTION

The present invention is directed to an intraluminal catheter having a catheter shaft and a distal member rotatable-relative to at least a section of the catheter shaft. In one embodiment, the catheter has-a catheter shaft, a distal member, which in a presently preferred embodiment is a balloon mounted on a distal portion of the shaft, and a tubular sealing member having an expandable portion disposed at least in part within a section of the distal member. The tubular sealing member has an expanded configuration, and an unexpanded configuration expandable into contact with the section of the distal member, so that the distal member is rotatable relative to at least a section of the catheter shaft and to the tubular sealing member when the tubular sealing member is in the unexpanded configuration. While discussed herein primarily in terms of a rotatable distal balloon, it should be understood that the distal member may be other operative members commonly provided on a catheter distal shaft section.

In one embodiment, the catheter shaft includes an outer tubular member defining an inflation lumen and having the tubular sealing member secured to a distal end of the outer tubular member, and an inner rotatable member rotatably disposed within the outer tubular member lumen when the tubular sealing member is in the unexpanded configuration. The inner rotatable member preferably extends distally out the distal end of the outer tubular member. In one embodiment, the balloon is disposed about and secured to a distal portion of the inner rotatable member, and the tubular sealing member radially expands into contact with a section of the balloon when pressure is introduced into the outer tubular member and tubular sealing member lumens. In a preferred embodiment, the balloon distal shaft is secured to the inner rotatable member prior to insertion into the patient's body lumen, however, the balloon distal shaft may be secured at any time after insertion as well. With the tubular sealing member in the unexpanded configuration, the balloon on the distal end of the catheter within a patient's body lumen can be rotated by torquing a proximal section of the inner rotatable member which extends outside of the patient. As a result, the inner rotatable member rotates relative to the outer tubular member, causing the balloon secured thereto to rotate. In a presently preferred embodiment, the tubular sealing member is disposed at least in part within a proximal shaft of the balloon. When inflation fluid is introduced into the inflation lumen, the tubular sealing member expands against the balloon proximal shaft, thus providing integrity between the inflation lumen and the balloon interior, allowing the balloon to be inflated. The tubular sealing member expands upon contact with the inflation fluid, preferably at a rate faster than the rate of balloon expansion, until it contacts the balloon shaft. At contact, the tubular sealing member secures, preferably releasably, to the balloon shaft, and seals the inflation lumen, effectively securing the rotatable balloon in a locked position for inflation. Thus, with the tubular sealing member in the expanded configuration, the balloon is typically not rotatable relative to the tubular sealing member. In one embodiment, a fluid tight seal is formed between the expanded tubular sealing member and the balloon proximal shaft.

In one embodiment, the catheter has an inflation lumen, a proximal shaft section, a distal shaft section having at least a portion which is-rotatable about the longitudinal axis of the catheter independent of the proximal shaft section, and a tubular sealing member having an expandable portion having an expanded configuration and an unexpanded configuration disposed within the distal shaft section of the catheter which radially expands into contact with the distal shaft section when inflation fluid is introduced into the inflation lumen.

In one embodiment, the catheter of the invention allows for a degree of translational (i.e., longitiudinal) movement in the rotatable member relative nonrotating shaft sections. Thus, in one embodiment, the inner rotatable member can be moved longitudinally relative to the outer tubular member, preferably when the tubular sealing member is in the unexpanded configuration.

The catheter of the invention may be configured for a variety of therapeutic or diagnostic uses such as balloon angioplasty, stent delivery, and drug delivery. In one embodiment, the catheter includes an angulated stent having a truncated end mounted on the balloon for delivery and deployment within a branch vessel of a patient's body lumen. In another embodiment, a drug delivery device may be placed on the distal end of a catheter. For example, a drug may be located on a stent carried by a balloon. The drug may be placed on only a portion of the delivery device and delivered to a specific area within the lumen. The delivery device may need rotation to properly align the drug delivery with the required location. Additionally, catheters without balloons may also be used in localized drug delivery.

The catheter of the invention provides improved ability to orient a distal operative section of the catheter in a desired orientation with the patient's body lumen. In the embodiment having a balloon which is rotatable relative to at least a section of the shaft, the balloon can be rotated relative to a section of the shaft to, for example, correctly orient a truncated end of a stent mounted on the balloon. In the embodiment having an outer tubular member and an inner member rotatable relative to the outer tubular member, the catheter of the invention has improved torqueability relative to conventional catheters in which the entire catheter shaft is torqued, because the surface area between the inner member and outer tubular member is less than the surface area between the outer member and the patient's vessel. Additionally, the coefficients of friction of the inner member and outer tubular member can be tailored in the catheter of the invention provide improved reduced friction between the inner and outer members. These and other advantages of the invention will become more apparent from the following detailed description and accompanying exemplary drawings.

DETAILED DESCRIPTION OF THE INVENTION

Figure 1:
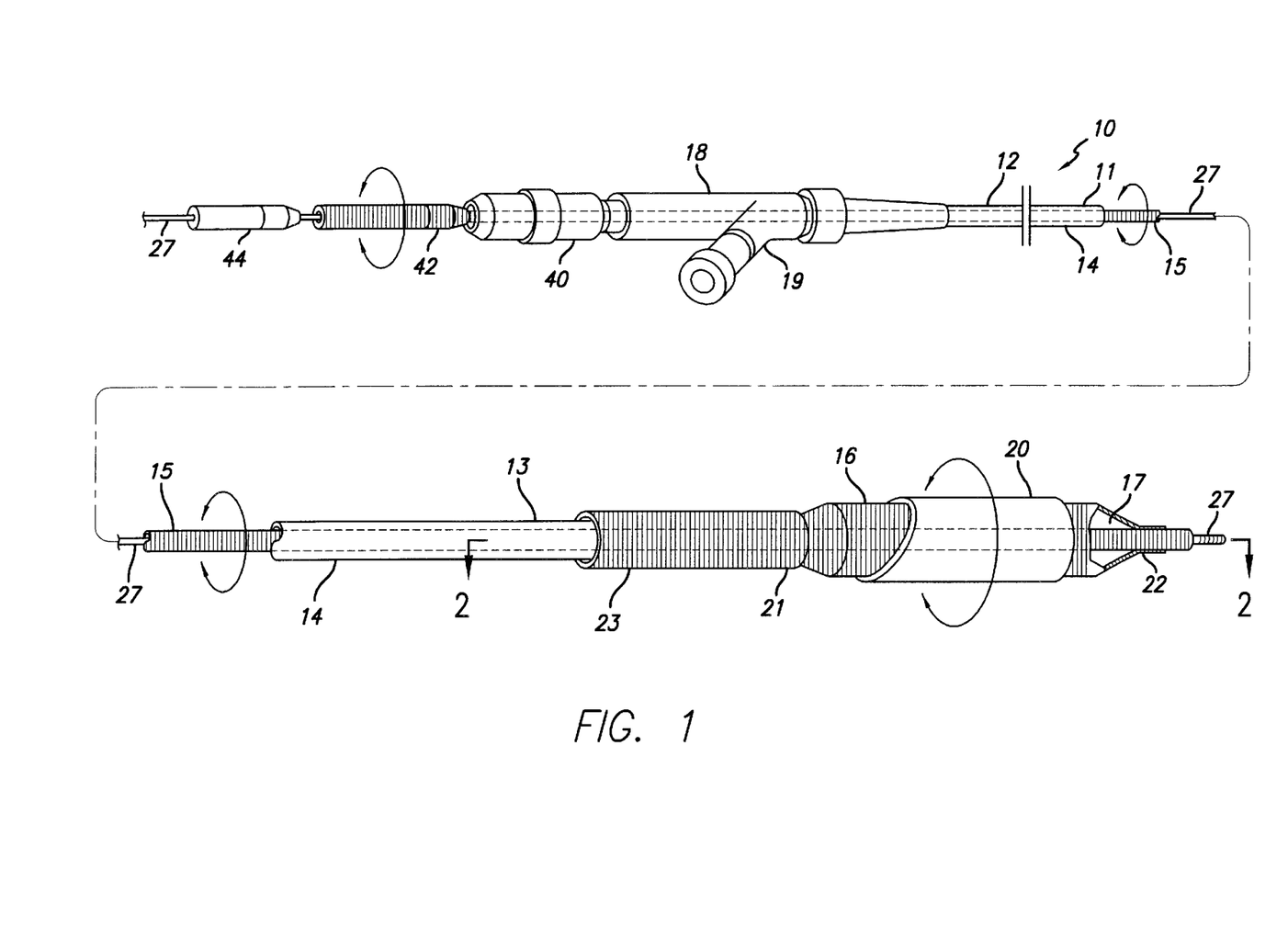
FIG. 1 is an elevational view of a catheter embodying features of the invention with the rotatable assembly shaded.

FIGS. 1–6 depict a catheter 10 embodying features of the invention generally including an elongated catheter shaft 11 having a proximal shaft section 12 and distal shaft section 13, an outer tubular member 14, an inner rotatable member 15 disposed within the outer tubular member 14, and inflatable and rotatable balloon 16 on the distal shaft section 13 of the catheter shaft 11. An adapter 18 is mounted on the proximal shaft section 12 of the catheter shaft 11 to direct inflation fluid to an inner chamber 17 of the inflatable balloon 16. The embodiment shown in FIG. 1 includes an angulated stent 20 disposed about the balloon 16. The inner rotatable member 15 and balloon 16 secured, illustrated as shaded regions of the catheter shown in FIG. 1, are rotatable about the longitudinal axis of the shaft 11 relative to the outer tubular member 14.

Figure 2:
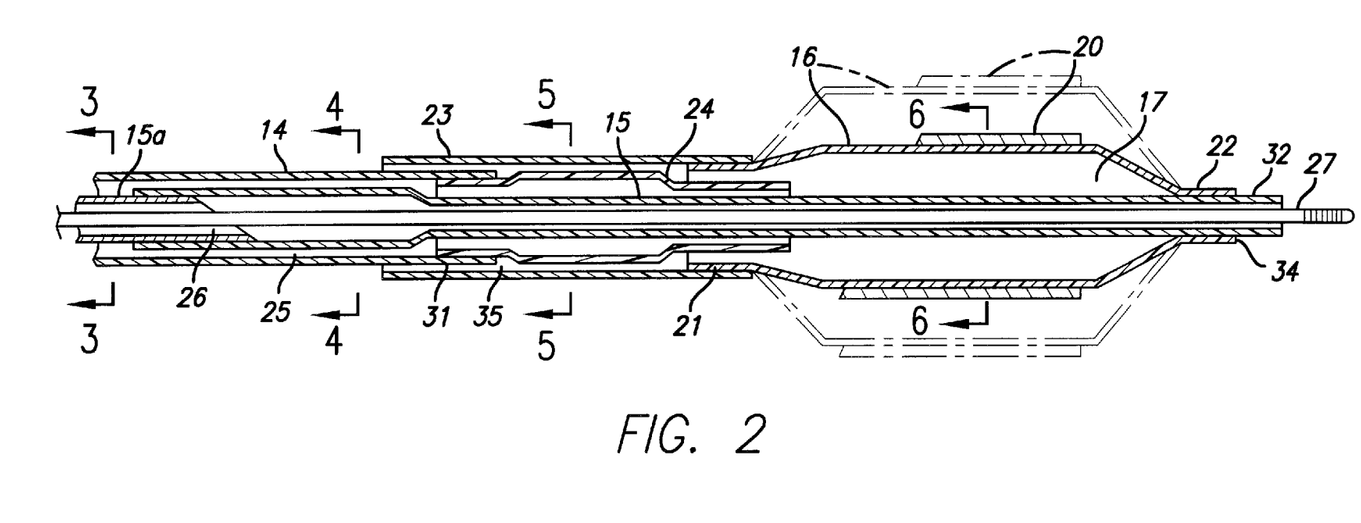
FIG. 2 is a longitudinal cross sectional view, partially in phantom, of the embodiment featured in FIG. 1 taken along the line 2—2.
Figure 3:
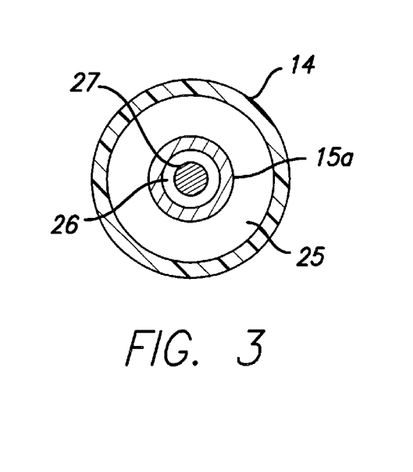
FIG. 3 is a transverse cross sectional view of the embodiment feature in FIG. 1 along the line 3—3.
Figure 4:
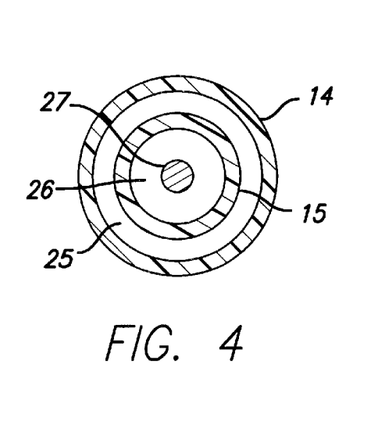
FIG. 4 is a transverse cross sectional view of the embodiment feature in FIG. 1 along the line 4—4.
Figure 5:
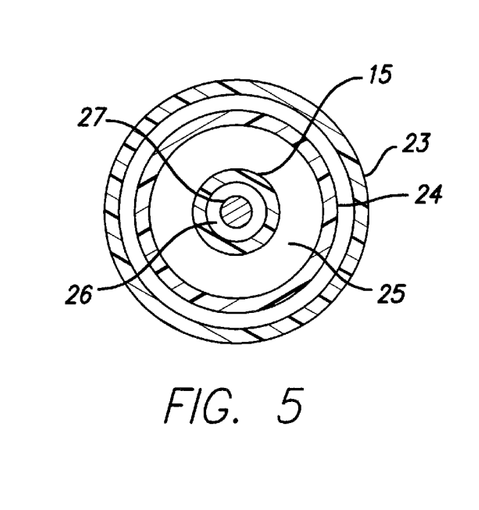
FIG. 5 is a transverse cross sectional view of the embodiment feature in FIG. 1 along the line 5—5.
Figure 6:
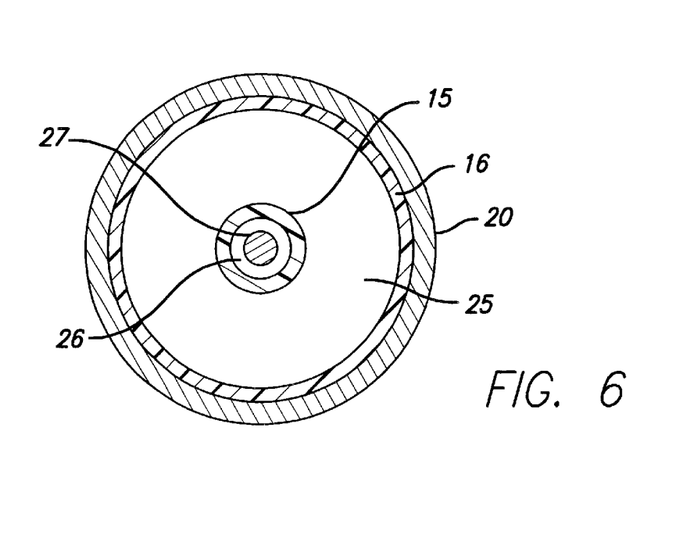
FIG. 6 is a transverse cross sectional view of the embodiment feature in FIG. 1 along the line 6—6.
Figure 7:
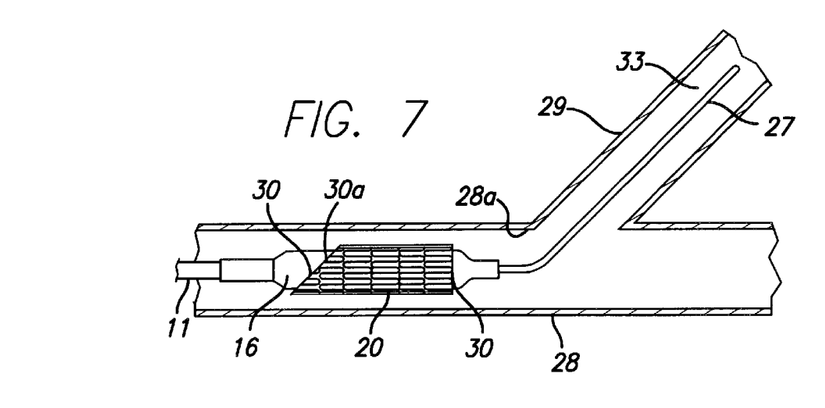
FIG. 7 is an elevational view of a catheter embodying features of the invention illustrated within a patient's body lumen.

FIG. 2 illustrates an enlarged longitudinal cross section of the balloon catheter 10 shown in FIG. 1, taken along line 2—2. The balloon 16 is rotatable about the catheter shaft 11 prior to inflation. The balloon 16 has a proximal shaft 21 and a distal shaft 22. The distal shaft 22 of the balloon 16 is secured to the inner rotatable member 15 at a distal location 34. In a preferred embodiment, the balloon distal shaft 22 is secured to the inner rotatable member distal location 34 prior to insertion into a patient's body lumen. In the embodiment illustrated in FIG. 2, the balloon proximal shaft 21 includes a balloon skirt 23. The balloon skirt 23 may be either an extension of the proximal shaft 21 or a separate component joined to the proximal shaft 21 with methods known in the art. In the illustrated embodiment, the balloon skirt 23 is a separate member secured to the proximal end of the balloon proximal shaft section 21. The terminology balloon proximal shaft should be understood to include the proximal shaft section 21, or section of the balloon formed by the proximal shaft section 21 and the balloon skirt 23. The proximal shaft 21 extends proximally from the balloon 16 and is preferably about 35 mm to about 45 mm long. The proximal shaft 21 has a wall thickness of about 0.006 inches to about 0.010 inches, preferably about 0.007 inches to about 0.009 inches and an inner diameter of about 0.035 inches to about 0.065 inches. The proximal shaft 21 may be formed of polyurethanes, polyolefins, polyesters, fluoropolymers, silicones, polymethacrylics, polyethers, polyvinyls, polyamides, polyethylene terephthalates, polybutylene terephthalates, elastomers, thermoplastic elastomers, rubbers, acetates and other polymeric materials, and co-polymers, blends, terpolymers and mixtures thereof or any combination of the materials listed. The proximal shaft 21 is preferably formed of a polyamide such as Nylon 12.

A tubular sealing member 24 is disposed within the catheter shaft 11. In a specific embodiment, the tubular sealing member 24 extends distally from the outer tubular member 14. In the embodiment illustrated in FIG. 2, the tubular sealing member 24 is a separate member secured to the distal end of the outer tubular member 14. However, the tubular sealing member 24 may alternatively be an extension of the outer tubular member 14 formed as an integral one piece member with the outer tubular member 14. In the embodiment of FIG. 2, the sealing member 24 is disposed within the balloon proximal shaft 21. The tubular sealing member 24 has an expanded configuration and an unexpanded configuration. In the embodiment illustrated in FIG. 2, the tubular sealing member 24 is illustrated in the unexpanded configuration prior to introduction of inflation fluid into the lumen 35 of the tubular sealing member 24. The balloon proximal shaft 21 has a rotatable configuration when the tubular sealing member 24 is in the unexpanded configuration. Before inflation, the balloon proximal shaft 21 is not sealingly secured to the outer member 14, and lumen 35 exists between the balloon proximal shaft 21 and the tubular sealing member 24.

An inflation fluid from a source of inflation fluid (not shown) is introduced through the arm 19 of the adapter 18. The inflation fluid travels throughout the inflation lumen 25 towards the distal shaft section of the catheter shaft 13. Upon the inflation fluid reaching the tubular sealing member 24, the tubular sealing member 24 expands in response to the radially expansive pressure of the inflation fluid therein or otherwise swells or expands in outer diameter to form the expanded configuration. The tubular sealing member 24 will expand until it meets the inner wall of the balloon proximal shaft 21. Once the tubular sealing member 24 meets the balloon proximal shaft 21, it releasably secures to the balloon proximal shaft 21. The tubular sealing member 24 expands more readily than any expansion in the balloon proximal shaft 21 in response to introduction of inflation media therein. In a presently preferred embodiment, the material forming at least an expandable portion of the tubular sealing member 21 is relatively softer, and thus more compliant, than the material of the balloon proximal shaft 21. In another embodiment (not shown), the tubular sealing member 24 has at least an expandable portion with a wall thickness less than the balloon proximal shaft 21. In a specific embodiment, the tubular sealing member 24 secures to the balloon proximal shaft 21 with a fluid tight, releasable seal. The proximal shaft of the balloon 21 is therefore no longer rotatable. In certain embodiments, the tubular sealing member 24 expands to meet the balloon skirt 23.

In the embodiment illustrated in FIG. 2, the tubular sealing member 24 extends at least partially within the balloon inflatable inner chamber 17. Alternatively, the tubular sealing member 24 distal end may be at or proximal to the distal end of the balloon proximal shaft 21. The tubular sealing member may have a length equal to, less than or greater than the length of the balloon proximal shaft 21. The tubular sealing member 24 may be formed of any suitable material, including aliphatic polyurethanes, low density polyethylene, thermoplastic polyurethane elastomers, aromatic polyurethanes, nylons and thermoplastic elastomers. Preferably, the tubular sealing member 24 is formed of an aliphatic polyurethane, a low density polyethylene or a thermoplastic polyurethane elastomer. Specific suitable materials that are commercially available include Pebax 40D, Estane® thermoplastic polyurethane from B.F. Goodrich, and Tecophilic medical grade aliphatic polyurethane from Thermedics, Inc. The sealing member 24 is preferably about 20 mm to about 30 mm long, specifically about 23 mm to about 25 mm. The inner diameter of the tubular sealing member is about 0.025 inches to about 0.030 inches, preferably about 0.028 inches prior to inflation. Upon inflation, the tubular sealing member expands to an inner diameter of about 0.045 to about 0.050 inches, preferably about 0.048 inches.

The outer tubular member 14 and inner rotatable member 15 therein define annular inflation lumen 25 therebetween. Inflation lumen 25 is in fluid communication with the interior chamber 17 of the inflatable balloon 16. The outer tubular member 14 has an outer distal length 31, and the inner. rotatable member 15 has an inner distal length 32. In certain embodiments, the outer distal length 31 is longitudinally proximal to the inner distal length 32 on the catheter shaft 11. The outer tubular member 14 has a wall thickness of about 0.007 inches to about 0.008 inches and an inner diameter of about 0.035 inches to about 0.045 inches, preferably an inner diameter of about 0.038 inches which flares to about 0.040 inches at the distal end.

In a specific embodiment, the inner rotatable member 15 is a tubular inner member. In the preferred embodiment, the inner rotatable member 15 defines an inner lumen 26 extending therein, which is configured to slidably receive a guidewire 27 suitable for advancement through a patient's arteries. In such a preferred embodiment as shown in.

FIGS. 1–6, the inner member would have a wall thickness of about 0.006 inches to about 0.008 inches, preferably about 0.007 inches and an inner diameter of about 0.015 inches to about 0.020 inches, preferably about 0.016 inches. However, the rotatable member 15 may also be a solid member, or a guidewire or other guiding member. In specific embodiments, the inner rotatable member 15 may have a portion of the member be a metal hypotube 15*a*. In embodiments including a metal hypotube 15*a*, the hypotube extends from the adapter and ends at least 30 cm proximal from the distal tip of the catheter shaft, preferably more than 30 cm. The rotatable member 15 may have no hypotube 15*a*, and instead comprises a coiled or braided support shaft that would thus avoid having a junction between a hypotube and distal section of the inner member (not shown). To the extent not discussed herein, the various catheter components can be formed of conventional materials commonly used in catheter construction. At least a section of the inner rotatable member may be formed of a metallic member such as a hypotube as discussed above, or may be formed of a polymeric material which may optionally have reinforcements such as braided polymeric or metallic members.

Figure 8:
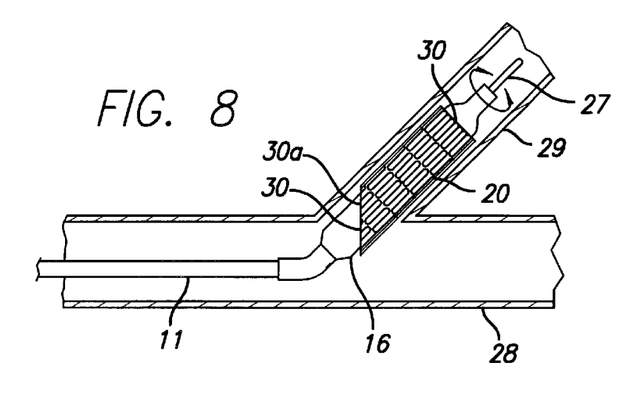
FIG. 8 is an elevational view of the catheter shown in FIG. 7, with the distal end of the catheter advanced with a branch body lumen with the stent out of alignment with the opening of the branch body lumen.

A method of performing a medical procedure is illustrated in FIGS. 7–10, generally comprising advancing a catheter 10 of the invention within a main body lumen 28 over a guidewire 27 and into an ostial branch lumen 29. The balloon 16 on the distal section 13 is then positioned so that at least a section of the balloon 16 is across a stenosed region 33 within the ostial branch lumen 29. FIG. 8 illustrates the problem faced with placement of the angulated stent 20. The angulated stent 20 has nonparallel transverse ends 30, with a truncated end 30*a* angled to match the angle of the opening of the branch lumen 29. In FIG. 8, the truncated, angular end of the stent 30a is not properly lined up with the main branch artery wall 28a. The inner rotatable member 15 is then rotated. In the embodiment illustrated in FIGS. 7–10, the balloon distal shaft 22 is secured to the inner rotatable member 15. When the inner rotatable member 15 is rotated, the balloon distal shaft 22 follows the rotation. The balloon proximal shaft 21 is rotatable, so the balloon 16 is rotated independent of the outer tubular member 14.

Figure 9:
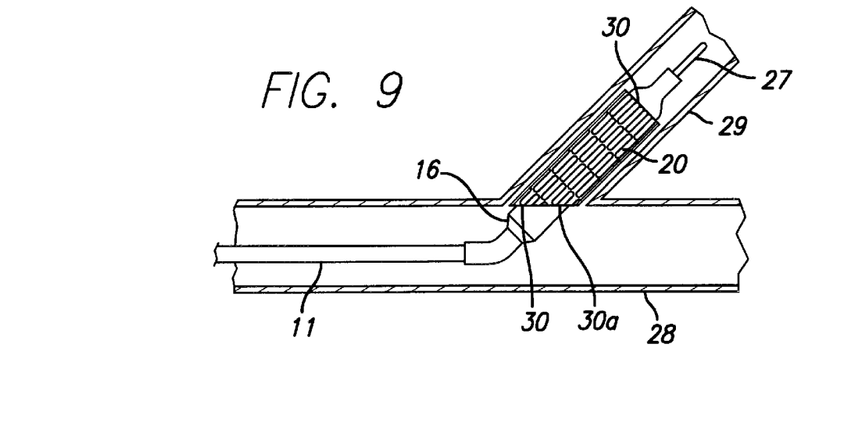
FIG. 9 is an elevational view of the catheter shown in FIG. 8 with the balloon rotated to correctly orient the stent within the branch body lumen.
Figure 10:
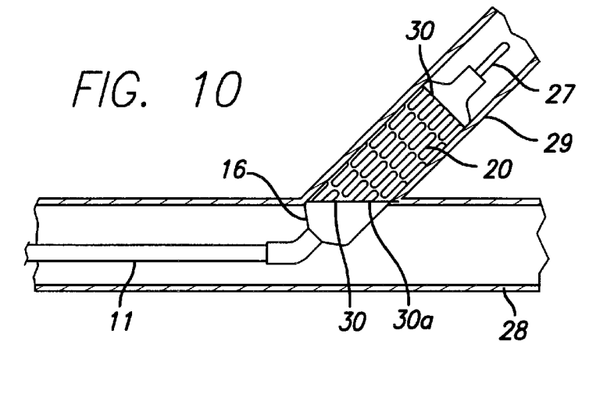
FIG. 10 is an elevational view of the catheter shown in FIG. 9 with the balloon and stent thereon expanded.

The stent 20 is properly lined up with the wall of the main branch artery 28a. The stent 20 alignment may be viewed with fluoroscopy by having the stent 20 be radiopaque or placing radiopaque markers on the stent 20, the balloon 16, or the inner rotatable member 15. Once the angulated stent 20 is aligned with the main branch artery 28 as shown in FIG. 9, the inflation fluid is introduced. The balloon proximal shaft 21 has a balloon skirt 23. The tubular sealing member 24 expands and engages the balloon skirt 23, thereby releasably securing the proximal shaft of the balloon 21 into position. The balloon 16 is then inflated against the patient's ostial lumen 29 to either dilate an undilated lesion or implant the stent 20.

In one embodiment, the tubular sealing member 24 in the unexpanded configuration allows for longitudinal movement of the inner rotatable member 15 and balloon 16 secured thereto, relative to the outer tubular member 14. Preferably, the longitudinal freedom of movement is limited to not greater than about the length of the tubular sealing member 24. In one embodiment, the inner rotatable member can be longitudinally displaced relative to the outer tubular member 14 about 1 mm to about 5 mm.

In the embodiment illustrated in FIG. 1, a valve or seal member 40 is connected to the side arm adapter 18 for sealing the inflation lumen 25, and a torque member 42 proximal to the seal member 40 is secured to the proximal end of the inner rotatable member 15. A guidewire torque member 44 is secured to the guidewire 27 to facilitate positioning the guide wire 27 during advancement within the body lumen. In a presently preferred embodiment, the seal member 40 comprises a cap and a compressive o-ring which surrounds the proximal end of the inner rotatable member 15. Once the balloon 16 is in a desired position in a body lumen, the cap is tightened to cause the o-ring to compress and thereby seal the inflation lumen. Preferably, the inner rotatable member 15 can be locked in position relative to the outer tubular member 14 by the seal member 40. Because the inner rotatable member 15 extends through the o-ring, the compressed o-ring prevents or inhibits longitudinal and rotational movement of the inner rotatable member 15, to facilitate stable placement of the balloon 16 during inflation thereof. The torque member 42 facilitates rotational control of the balloon 16. Specifically, with the proximal end of the outer tubular member 14 secured to the side arm adapter 18 and the torque member 42 secured to the inner rotatable member 15, rotating the torque member 42 causes the inner rotatable member to transmit the movement to the balloon 16. Similarly, the seal member 40 and torque member 42 are configured to allow longitudinal movement of the inner rotatable member 15 relative to the outer tubular member 14 as discussed above. In one embodiment, the torque member 42 is longitudinally displaceable relative to the seal member 40 without rotating the torque member 42, so that the inner rotatable member 15 can be rotated without being longitudinally displaced, and visa versa. In the embodiment illustrated in FIG. 1, the torque member 42 distal end is configured to be positioned within the proximal port of the seal member 40.

The intravascular catheter 10 depicted in FIGS. 1–6 is an over-the-wire catheter. However, any catheter would benefit from the invention, including rapid exchange catheters and drug delivery catheters. Rapid exchange catheters typically comprise an elongated shaft with a proximal end, a distal end, a balloon on a distal shaft section in fluid communication with an inflation lumen, a distal guidewire port in a distal end of the catheter, and a proximal guidewire port spaced a substantial distance from the proximal end of the catheter so that the proximal guidewire port is closer to the distal guidewire port than to the proximal end of the catheter, and a short guidewire lumen extending between the proximal and distal guidewire ports.

While discussed in terms of certain preferred embodiments, those skilled in the art that various modifications and improvements may be made without departing from the scope thereof. For example, the specific dimensions of the catheter components will vary depending on the desired use of the catheter, materials, balloon size, tolerances, and the like. Moreover, although individual features of embodiments of the invention may be shown in some of the drawings and not in others, those skilled in the art will recognize that individual features of one embodiment of the invention can be combined with any or all the features of another embodiment.

What is claimed is:

1. A balloon catheter, comprising:
  a. an elongated catheter shaft having a proximal shaft section, a distal shaft section, and an inflation lumen extending within at least a portion of the catheter shaft;
  b. a balloon mounted on a portion of the distal shaft section, having a proximal shaft, a distal shaft, a working section, and an inflatable interior chamber in fluid communication with the inflation lumen; and
  c. a tubular sealing member having an expandable portion disposed at least in part within the balloon proximal shaft, having an expanded configuration, and an unexpanded configuration expandable into contact with the balloon proximal shaft.

2. The balloon catheter of claim 1 wherein the balloon is rotatable about the tubular sealing member when the tubular sealing member is in the unexpanded configuration.

3. The balloon catheter of claim 1 wherein the expanded configuration of the tubular sealing member is formed by the introduction of inflation media into the tubular sealing member lumen, to releasably secure the tubular sealing member to the balloon proximal shaft.

4. The balloon catheter of claim 3 wherein the tubular sealing member expands to form a fluid tight seal against the balloon proximal shaft.

5. The catheter of claim 1 wherein the catheter shaft has an inner rotatable member rotatable when the tubular sealing member is in the unexpanded configuration.

6. The catheter of claim 5 wherein the inner rotatable member defines at least in part a guidewire lumen.

7. The balloon catheter of claim 5 wherein the balloon distal shaft is sealingly secured to the inner rotatable member.

8. The catheter of claim 5 including an outer tubular member disposed about the inner rotatable member and defining at least in part the inflation lumen which is in fluid communication with the interior chamber of the balloon, and wherein the inner rotatable member and balloon secured thereto are rotatable relative to the outer tubular member when the tubular sealing member is in the unexpanded configuration.

9. The catheter of claim 8 wherein the tubular sealing member has proximal and distal ends, and a lumen therein in fluid communication with the inflation lumen, and is disposed about the inner rotatable member, and is secured by its proximal end to a distal portion of the outer tubular member.

10. The catheter of claim 1 wherein the balloon proximal shaft comprises a balloon skirt.

11. The catheter of claim 10 wherein the balloon skirt proximal end is proximal to a proximal end of the tubular sealing member.

12. The balloon catheter of claim 1 wherein the tubular sealing member extends at least partially into the balloon inflatable interior chamber.

13. The balloon catheter of claim 1 wherein the tubular sealing member is formed of a material selected from the group consisting of aliphatic polyurethanes, aromatic polyurethanes, thermoplastic elastomers, low density polyethylene and thermoplastic polyurethane elastomers.

14. The balloon catheter of claim 1 wherein the balloon comprises at least one layer having channels configured for drug delivery.

15. The balloon catheter of claim 3 wherein the catheter shaft inner rotatable member has a wall thickness of about 0.004 inches to about 0.010 inches.

16. The balloon catheter of claim 3 wherein the catheter shaft inner rotatable member has an inner diameter of about 0.015 inches to about 0.020 inches.

17. The balloon catheter of claim 4 wherein the catheter shaft outer member has a wall thickness of about 0.007 inches to about 0.008 inches.

18. The balloon catheter of claim 4 wherein the catheter shaft outer member has an inner diameter of about 0.035 inches to about 0.045 inches.

19. The balloon catheter of claim 1 wherein the balloon proximal shaft has a wall thickness of about 0.003 inches to about 0.010 inches.

20. The balloon catheter of claim 1 wherein the balloon proximal shaft has an inner diameter of about 0.035 inches to about 0.065 inches.

21. The balloon catheter of claim 6 wherein the balloon skirt has a length of about 15 mm to about 45 mm.

22. The balloon catheter of claim 1 wherein the tubular sealing member has a length of about 5 mm to about 40 mm.

23. The balloon catheter of claim 1 wherein the tubular sealing member has an inner diameter of about 0.025 inches to about 0.030 inches before expansion.

24. The balloon catheter of claim 1 wherein the balloon is longitudinally displaceable relative to the tubular sealing member when the tubular sealing member is in the unexpanded configuration.

25. A balloon catheter assembly, comprising:
a. an elongated catheter shaft having a proximal shaft section, a distal shaft section, and an inflation lumen extending within at least a portion of the catheter shaft;
b. a balloon mounted on a portion of the distal shaft section, having a proximal shaft, a distal' shaft, a working section, and an inflatable interior chamber in fluid communication with the inflation lumen;
c. a tubular sealing member having an expandable portion disposed at least in part within the balloon proximal shaft, having an expanded configuration, and an unexpanded configuration expandable into contact with the balloon proximal shaft; and
d. a stent disposed about at least a section of the balloon.

26. The balloon catheter assembly of claim 25, wherein the stent is an angular stent having a truncated end.

27. A balloon catheter, comprising:
a) a catheter shaft having a proximal end, a distal end, an inner rotatable member, an outer tubular member having an inflation lumen therein; and
b) a balloon disposed about a distal section of the catheter shaft having a balloon proximal shaft which is configured to be rotatable relative to the outer tubular member about the catheter shaft longitudinal axis, and a balloon distal shaft sealingly secured to a distal portion of the inner rotatable member.

28. The balloon catheter of claim 27 wherein the catheter further comprises an expandable member secured to the catheter shaft, extending within at least a section of the balloon proximal shaft.

29. The balloon catheter of claim 27 wherein the expandable member has an expanded configuration, and an unexpanded configuration, and wherein the balloon proximal shaft is rotatably disposed about the expandable member when the expandable member is in the unexpanded configuration.

30. The balloon catheter of claim 27 including a first adapter secured to the proximal end of the outer tubular member, and a torque member adapter secured to the proximal end of the inner rotatable member configured to be rotatable relative to the first adapter, and longitudinally displaceable relative to the first adapter without being rotated, so that the inner rotatable member is rotatable relative to the outer tubular member and independently longitudinally displaceable relative to the outer tubular member.

* * * * *

UNITED STATES PATENT AND TRADEMARK OFFICE
CERTIFICATE OF CORRECTION

PATENT NO. : 6,540,719 B2
DATED : April 1, 2003
INVENTOR(S) : Stephen J. Bigus et al.

It is certified that error appears in the above-identified patent and that said Letters Patent is hereby corrected as shown below:

<u>Title page,</u>
Item [56], U.S. PATENT DOCUMENTS, add:
-- 5,549,580    1/1995    Diaz
5,042,985    5/1989    Elliott et al.
6,162,246    2/1999    Barone
5,279,561    2/1992    Roucher et al.
6,139,525    7/1997    Davis-Lemessy et al.
5,279,562    1/1993    Sirhan et al.
6,238,430 B1  8/1999    Klumb et al.
5,501,667    3/1994    Verduin Jr.
5,919,163    7/1997    Glickman --.

Signed and Sealed this

Sixteenth Day of September, 2003

JAMES E. ROGAN
*Director of the United States Patent and Trademark Office*